(12) United States Patent
Scoggins

(10) Patent No.: US 6,860,263 B1
(45) Date of Patent: Mar. 1, 2005

(54) BAND NASAL DILATOR

(76) Inventor: Al Scoggins, 935 Hillside Mill Dr., Grayson, GA (US) 30017-1905

( * ) Notice: Subject to any disclaimer, the term of this patent is extended or adjusted under 35 U.S.C. 154(b) by 0 days.

(21) Appl. No.: 10/619,952

(22) Filed: Jul. 15, 2003

(51) Int. Cl.7 ............................................. A61M 15/00
(52) U.S. Cl. ........................ 128/200.24; 128/206.25; 606/199
(58) Field of Search ................... 128/200.26, 206.11, 128/206.25, 207.11, 207.17, 912, DIG. 26, 858, 200.24; 606/198, 199, 204.45; 602/5

(56) References Cited

U.S. PATENT DOCUMENTS

| | | | | |
|---|---|---|---|---|
| 186,422 A | * | 1/1877 | Hackett et al. | 128/866 |
| 1,232,956 A | * | 7/1917 | Mooney | 606/199 |
| 2,245,969 A | * | 6/1941 | Francisco et al. | 128/207.18 |
| 2,590,006 A | * | 3/1952 | Gordon | 604/180 |
| 2,735,432 A | * | 2/1956 | Hudson | 128/207.18 |
| 3,426,751 A | * | 2/1969 | Radewan | 606/204.45 |
| 3,677,250 A | * | 7/1972 | Thomas | 604/180 |
| 3,804,083 A | * | 4/1974 | Tupper | 606/204.35 |
| 4,191,180 A | * | 3/1980 | Colley et al. | 128/207.17 |
| 4,402,314 A | * | 9/1983 | Goode | 606/204.45 |
| 4,774,935 A | * | 10/1988 | Aronsohn | 606/204.45 |
| 4,867,154 A | * | 9/1989 | Potter et al. | 128/207.17 |
| 5,362,303 A | * | 11/1994 | Jasen et al. | 602/17 |
| 5,383,451 A | * | 1/1995 | DeIulio | 128/207.17 |
| 5,806,525 A | * | 9/1998 | Pope, Jr. | 128/848 |
| 5,890,486 A | * | 4/1999 | Mitra et al. | 128/200.24 |
| 5,913,873 A | * | 6/1999 | Blach et al. | 606/204.45 |
| 6,006,746 A | * | 12/1999 | Karell | 128/200.24 |
| 6,050,263 A | * | 4/2000 | Choksi et al. | 128/207.14 |
| 6,067,985 A | * | 5/2000 | Islava | 128/207.17 |
| 6,068,649 A | * | 5/2000 | Chamberlain | 606/234 |
| 6,092,521 A | * | 7/2000 | Miura | 128/201.13 |
| 6,238,411 B1 | * | 5/2001 | Thorner | 606/199 |

* cited by examiner

Primary Examiner—Aaron J. Lewis
(74) Attorney, Agent, or Firm—Hinkle & O'Bradovich, LLC

(57) ABSTRACT

A banded nasal dilator is described. In a typical embodiment, the banded nasal dilator includes an elongated band that can wrap around the back of a user's head. Each end of the band includes a face pad having an adhesive portion that is adapted to connect to the user's cheek. A protective tab covers the adhesive portion until the dilator is ready for use, at which time the tab can be removed to expose the adhesive portions of the face pads. In one embodiment, each face tab can include an upper and lower strip that enclose an end of the band.

2 Claims, 2 Drawing Sheets

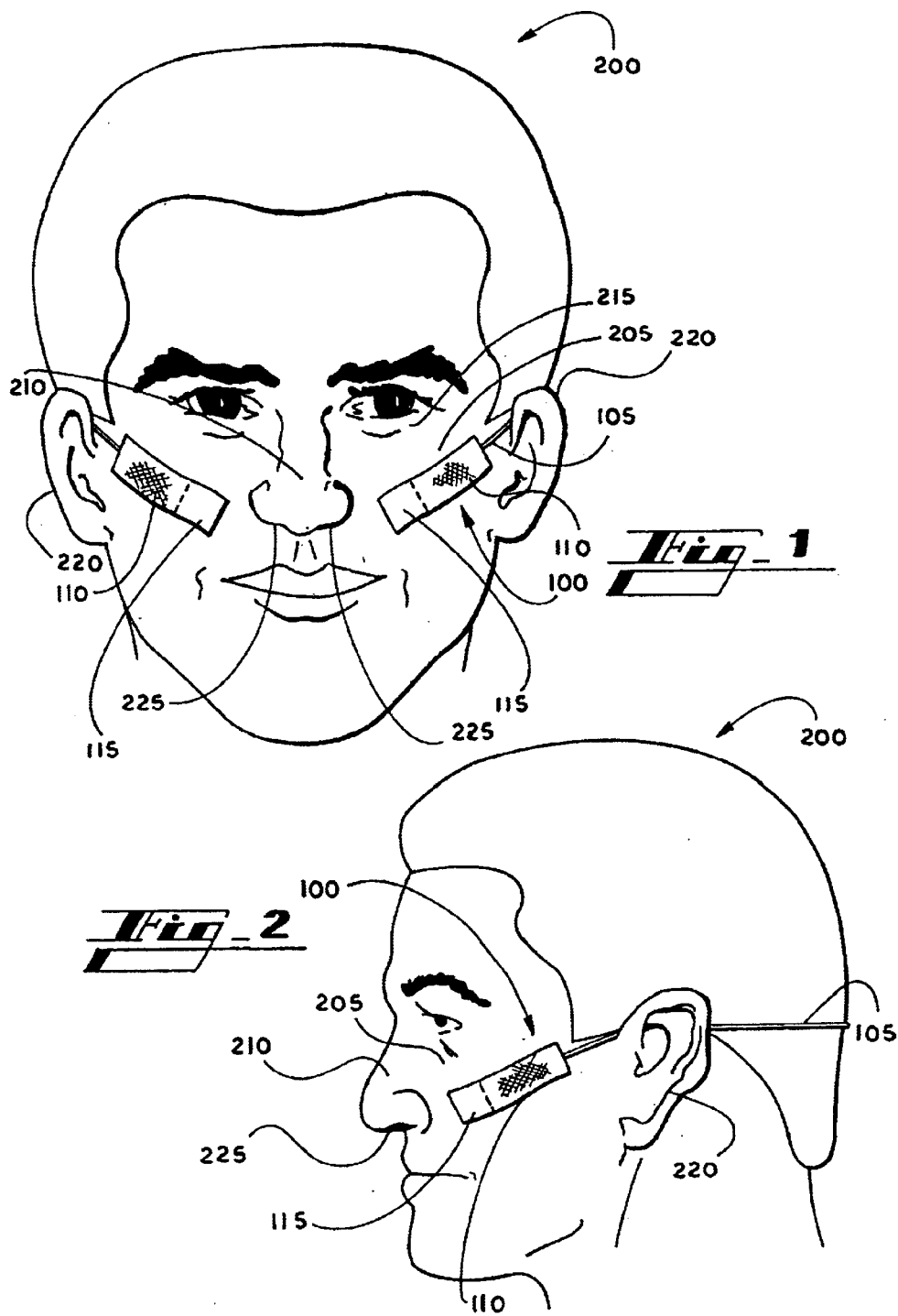

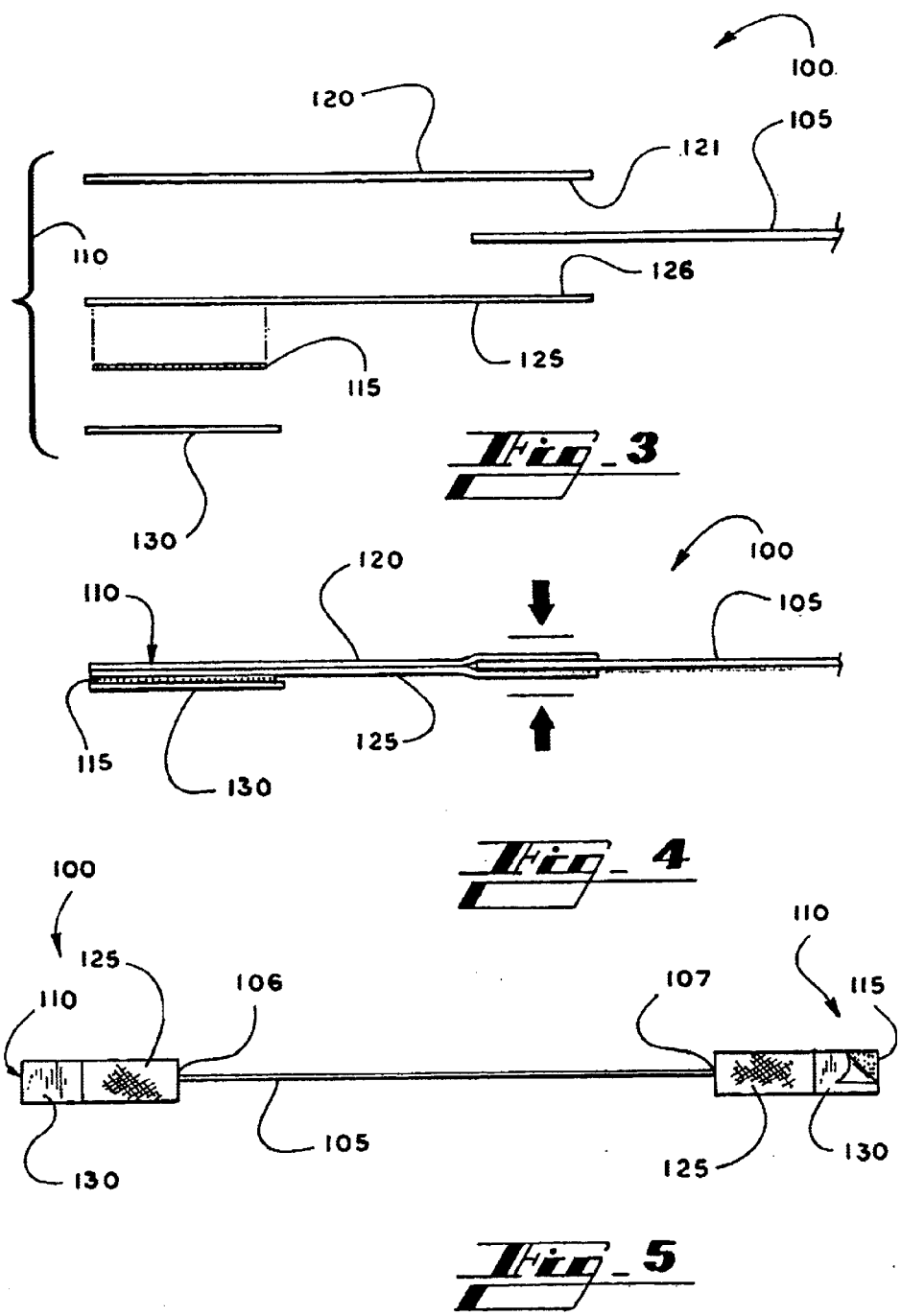

BAND NASAL DILATOR

BACKGROUND

I. Field of the Invention

The present invention relates generally to the field of breathing aids, and, more particularly to a banded nasal dilator apparatus, system and method.

II. Description of the Related Art.

Many people suffer from a variety of breathing problems from restricted nasal passages that can be temporarily relieved by mechanical devices. Such breathing problems are typically experienced by people with deviated septa, colds, congestion and by those people who snore. The temporary mechanical relief can be obtained by wearing a nose mounted dilator. These nose mounted dilators typically include a resilient bar having an adhesive portion on either end. The adhesive portion is exposed and attached to skin on either side of the nose, which bends the bar. Since the bar is resilient it attempts to spring back into a straightened state, which in turn pulls on the nose skin. This pulling helps to open the nasal (nostril) passages thereby providing breathing relief to the user. However, the adhesive on these nose mounted dilators tends to give out in short periods of time, thereby releasing the bar from its secured location on the nose. The adhesive tends to give out due to losing sticking power from oils on the nose. Furthermore, since the bar is resilient, it constantly pulls on the adhesive in a perpendicular or normally directed force away from the skin. In addition, those people who use the nose mounted dilators during exercise tend to lose the dilators faster due to profuse sweating.

SUMMARY

In general, the invention features a banded nasal dilator that connects to the user on or about the cheek area rather than on the nose. A band wraps around a portion of a user's head. Each end of the band includes a face pad that connects to each cheek. The band can maintain a tension force that provides a tangential force on each of the pads that pulls on the cheek skin. The pull on the cheek skin provides a pull on the nostrils, which are gently dilated thereby enabling easier breathing by opening the nasal passages.

In general, in one aspect, the invention features a nasal dilator apparatus, including an elongated band having a first end and a second end and a face pad connected to each of the first and second ends.

In one implementation, the apparatus further includes an adhesive portion connected to one end of each of the face pads.

In another implementation, the apparatus further includes a protective tab covering each of the adhesive portions.

In another implementation, each of the face pads includes an upper strip having an inner surface and a lower strip having an inner surface and connected to the upper strip, the inner surfaces being generally connected and opposed, wherein the upper and lower strips enclose an end of the band.

In another aspect, the invention features a nasal dilator kit, including an elongated head band adapted to generally wrap around a user's head, and fit above the user's ears, a face pad connected to each end of the band, the face pad including an upper planar strip and a lower planar strip, the strips enclosing an end of the band, an adhesive portion connected to an end of the lower strip opposite the end of the lower strip connected to the end of the band and a protective tab covering the adhesive portion, the tab being adapted to be removed from the adhesive portion and discarded, wherein the adhesive portion is adapted to connect to the face of the user.

In still another aspect, the invention features a method of dilating nasal passages, including providing a first pad having an adhesive portion covered by a protective tab and adapted to connect to a user's face providing a second pad having an adhesive portion covered by a protective tab and adapted to connect to a user's other cheek adjacent the user's nose, providing a band connected between the pads and positioned around the user's head, the band providing a tension force between the pads, removing the tab on the first pad to expose the adhesive portion, placing the adhesive portion of the first pad on one cheek adjacent the user's nose, providing a tension in the band, placing the band in a desired location around the user's head, removing the tab on the second pad to expose the adhesive portion and placing the adhesive portion of the second pad on the other cheek adjacent the user's nose.

In still another aspect, the invention features a method of opening nasal passages to provide easier breathing through the nose, including providing a tangential force on a users cheek skin on either side of the user's nose.

One advantage of the invention is that it creates a substantially increased volume of air in people with restricted nasal passages without being attached to the nose in anyway.

Another advantage of the invention is that the adhesive portions of the apparatus do not lose their adhesive power due to secreted skin oils on the nose and typically remains in place overnight or as long as desired.

Another advantage of the invention is that the apparatus typically remains in place during exercise routines that result in profuse sweating.

Other objects, advantages and capabilities of the invention will become apparent from the following description taken in conjunction with the accompanying drawings showing the preferred embodiment of the invention.

BRIEF DESCRIPTION OF THE DRAWINGS

FIG. 1 illustrates a front view of a user's head having an embodiment of a banded nasal dilator apparatus;

FIG. 2 illustrates a side view of a user's head having an embodiment of a banded nasal dilator apparatus;

FIG. 3 illustrates a partial side view of constituent components of an embodiment of a banded nasal dilator apparatus;

FIG. 4 illustrates a partial side view of an embodiment of a banded nasal dilator apparatus; and FIG. 5 illustrates a top view of an embodiment of a banded nasal dilator apparatus.

DETAILED DESCRIPTION

In general, the apparatus provides a band that wraps around a portion of a user's head. Each end of the band includes a face pad that connects to each cheek. The band can maintain a tension force that provides a tangential force on each of the pads that pulls on the cheek skin. The pull on the cheek skin provides a pull on the nostrils, which are gently dilated thereby enabling easier breathing by opening the nasal passages.

Referring to the drawings wherein like reference numerals designate corresponding parts throughout the several figures, reference is made first to FIG. 1 that illustrates a front view of a user's head 200 having an embodiment of a banded nasal dilator apparatus 100. The apparatus 100 typically includes a band 105 that wraps around the back of the user's head 200. The apparatus 100 further includes pads 110 that can be connected to the user's cheeks 205 by an adhesive portion 115.

FIG. 2 illustrates a side view of a user's head having an embodiment of a banded nasal dilator apparatus 100. As described above with respect to FIG. 1, the band 105 generally wraps around the user's head 200 and adhesive portions 115 of the pads 110 connect to the user's cheek 205.

FIG. 3 illustrates a partial side view of constituent components of an embodiment of a banded nasal dilator apparatus 100. As described above, the apparatus typically includes a band 105, each end of the band being connected to a pad 110. In one embodiment, the pad 110 can include an upper planar strip 120 and a lower planar strip 125, each of the strips 120, 125 being connected at one end to the band 105. The strips 120, 125 each have a respective inner surface 121, 126 facing the end of the band 105. The apparatus 100 also can include the adhesive portion 115 connected to one end of the lower planar strip 125 opposite the end of the lower planar strip 125 connected to the band 105. A protective tab 130 is typically connected to the adhesive portion 115. It is understood that the tab 130 is of the type that can cover and protect adhesive but not detrimentally affect the adhesive.

FIG. 4 illustrates a partial side view of an embodiment of a banded nasal dilator apparatus 100. As described above, the apparatus typically includes a band 105, each end of the band being connected to the pad 110 having the upper planar strip 120 and the lower planar strip 125, each of the strips 120, 125 being connected at one end to the band 105. The inner surfaces 121, 126 are generally connected to each other. The apparatus 100 generally also includes the adhesive portion 115 connected to one end of the lower planar strip 125 opposite the end of the lower planar strip 125 connected to the band 105. The protective tab 130 is typically connected to the adhesive portion 115. In general, one end of the pad 110 formed by the upper and lower strips 120, 125 enclose one end of the band 105. This enclosure secures the ends of the band 105 to the pads 110. The strips 120, 125 can be secured to each other by a layer of adhesive between the strips or by a variety of other fasteners. In another embodiment, the strips 120, 125 can also be a single integral piece folded upon itself, each end of the single integral piece thereby enclosing the ends of the band 105.

In a specific embodiment, the band 105 can be a cylindrical, elastic, clear plastic or polymer. The upper and lower strips 120, 125 can be adhesive backed, breathable hypoallergenic cloth tape that can be readily found in medical supply shops. It is understood that this specific embodiment does not limit the scope of the other embodiments described herein.

FIG. 5 illustrates a top view of an embodiment of a banded nasal dilator apparatus 100. Each end 106, 107 of the band 105 is connected to a respective face pad 110. The lower strips 125 of each of the pads 110 is shown having the protective tabs 130 connected to the adhesive portions 115. The pad 130 adjacent to the end 107 of the band 105 is shown partially folded illustrating its removal to expose the adhesive portion 115.

Referring again to FIGS. 1 and 2, the apparatus 100 is worn by removing one of the protective tabs 130 from either of the face pads 110 and placing the exposed adhesive portion 115 to the right or left of the nose 210 underneath the eyelid 215 on the same side. The face pad 110 generally rests on the cheek bone of the user. The end of the face pad 110 having the adhesive portion 115 generally becomes a fixed end. The band 105 is generally positioned above the ear 220 of the same side. In a typical implementation, the band 105 generally intersects the head 200 in the same location at which an eyeglass temple would contact. The user can then pull the band 105 by grasping the remaining face pad 110 around the back side of the head 200 while ensuring that the band 105 on the remaining side of the apparatus 100 generally follows a similar path as the first side. The user can then remove the remaining protective tab 130 to expose the other adhesive portion 115. The user then can apply a suitable tension to the apparatus 100 by pulling on the band 105, which is placed over the ear 220 similarly as the first ear 220, while grasping the remaining pad 110 with the exposed adhesive portion 115. The user then places the remaining pad on a similar location to the side of the nose 210 and under the eyelid 215. The resulting tension of the band 105 causes the face pads 110 to gently move the nostrils outward generally toward the ears 220 thereby creating a dilation in both nostrils and thus the nasal passages.

In general, the face pads 110 have a tension along a line following the surface of the user's facial skin. This force is generally tangential to the adhesive portion 115 and therefore makes it more difficult to release from the face due to oils and perspiration, in contrast to nose mounted dilators that typically result in a more perpendicular or normally directed force on the respective adhesive portions. In addition, the planar strips 120, 125 allow an even distribution of forces along the face pads 110. Furthermore, in general, the area of the face in contact with the adhesive portions 115 of the face pads 110 are not as prone to have the amount of skin oils present on nose skin. Adhesion tends to be more evenly attained and uniform and allows the apparatus 100 to remain secure for prolonged periods of time.

In general, many modifications can be made in the above-described embodiments without departing from the spirit of the invention. For example, the pads 110 and the upper and lower strips 120, 125 are shown to be elongated rectangles. It is understood that a variety of other shapes are contemplated. Furthermore, the band 105 and the pads 110 can be a single integral piece of the same material. In general, the upper and lower strips 120, 125 are illustrated as mechanically attaching to and securing the ends of the band 105. Other mechanical fastening mechanisms and devices are contemplated. For example, each pad 10 can include a metal tab through which an end of the band 105 can fit.

In general, the band has been described to fit around the back of the user's head. It is understood that other user's may desire to place the bands in many ways. For example, the band could be placed under the ears and around the back of the head. The band could also be placed under the ears then around the top of the user's head.

In general, it is understood that suitable methods for pulling the skin on the cheeks, for example adjacent or juxtaposed to the nose, to dilate the nostrils and nasal passages are contemplated. For example, a rigid band can be placed around the head and on the cheeks adjacent the nose to gently pull the cheek skin from the nostrils to open the nasal passages. Furthermore, it is understood that the use of a tangential force along the skin is typically contemplated to open the nasal passages.

Therefore, the foregoing is considered as illustrative only of the principles of the invention. Further, various modifications may be made of the invention without departing from the scope thereof and it is desired, therefore, that only such limitations shall be placed thereon as are imposed by the prior art and which are set forth in the appended claims.

What is claimed is:

1. A nasal dilator kit, comprising:
   an elongated head band adapted to generally wrap around a user's head, and fit above the user's ears;
   a face pad connected to each end of the band, the face pad comprising:
   an upper planar strip and a lower planar strip, the strips enclosing an end of the band;
   an adhesive portion connected to an end of the lower strip opposite the end of the lower strip connected to the end of the band; and
   a protective tab covering the adhesive portion, the tab being adapted to be removed from the adhesive portion and discarded, wherein the adhesive portion is adapted to connect the to the face of the user.

2. A method of dilating nasal passages, comprising:
   providing a first pad having an adhesive portion covered by a protective tab and adapted to connect to a user's cheek;
   providing a second pad having an adhesive portion covered by a protective tab and adapted to connect to a user's other cheek adjacent the user's nose;
   providing a band connected between the pads and positioned around the user's head, the band providing a tension force between the pads;
   removing the tab of the first pad to expose the adhesive portion;
   placing the adhesive portion of the first pad on one cheek adjacent the user's nose;
   providing a tension in the band;
   placing the band in a desired location around the user's head;
   removing the tab on the second pad to expose the adhesive portion; and
   placing the adhesive portion of the second pad on the other cheek adjacent the user's nose.

* * * * *